United States Patent [19]
Mori et al.

[11] Patent Number: 5,575,986
[45] Date of Patent: Nov. 19, 1996

[54] CHELATING AGENT, COMPLEX COMPOUND OF SAID CHELATING AGENT AND METALLIC ATOM, AND DIAGNOSTIC AGENT COMPRISING SAME

[75] Inventors: Fumio Mori; Tadashi Okano; Kazuki Murakami; Masakazu Shintome; Hiromichi Mukai; Ikuko Miyagi; Takashi Imagawa; Sang-Won Kim, all of Osaka; Taro Marukawa, Nagoya; Takahiro Kozuka, Kobe, all of Japan

[73] Assignee: The Green Cross Corporation, Osaka, Japan

[21] Appl. No.: 423,451

[22] Filed: Apr. 19, 1995

Related U.S. Application Data

[63] Continuation of Ser. No. 204,164, Mar. 3, 1994, Pat. No. 5,453,264.

[30] Foreign Application Priority Data

Jul. 3, 1992 [JP] Japan ................. 4-200392

[51] Int. Cl.⁶ .......................... A61K 49/00; A61K 31/32; A61K 31/295
[52] U.S. Cl. .................. 424/9.364; 436/173; 514/492; 514/502; 534/16; 556/1; 556/148; 562/565; 562/566; 424/9.42; 424/9.5
[58] Field of Search ............................ 424/9; 556/1, 148; 534/16; 514/492, 502; 562/565, 566; 436/173

[56] References Cited

U.S. PATENT DOCUMENTS 5,138,039  8/1992  Seri et al. .

FOREIGN PATENT DOCUMENTS

| 0413405 | 2/1991 | European Pat. Off. . |
| 0450742 | 10/1991 | European Pat. Off. . |
| 3173856 | 7/1991 | Japan . |
| 3291260 | 12/1991 | Japan . |
| WO9211232 | 7/1992 | Japan . |
| WO9303351 | 2/1993 | Japan . |
| 5186372 | 7/1993 | Japan . |
| 5229998 | 9/1993 | Japan . |

*Primary Examiner*—Porfirio Nazario-Gonzales
*Attorney, Agent, or Firm*—Sughrue, Mion, Zinn, Macpeak & Seas

[57] ABSTRACT

A compound of the following formula

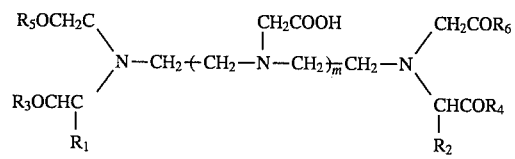

wherein m is an integer of 1 to 3, $R_1$ and $R_2$ are the same or different and each is hydrogen atom or lower alkyl, and $R_3$, $R_4$, $R_5$ and $R_6$ are the same or different and each is hydroxy or a group of the formula

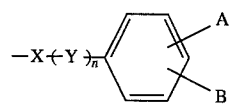

(wherein n is 0 or 1, X is —NH— or —O—, Y is alkylene, A is hydrogen atom, lower alkyl, lower alkoxy, halogen atom or trifluoromethyl, and B is alkyl or alkenyl), with the proviso that two or three of $R_3$, $R_4$, $R_5$ and $R_6$ are hydroxyl groups and that when two of them are hydroxyl groups, the cases where $R_3$ and $R_5$ are hydroxy, and $R_4$ and $R_6$ are hydroxy are excluded; a complex compound comprising said compound and a metallic atom; and a diagnostic agent containing said complex compound. The above compound is useful as a chelating agent and the complex compound comprising said compound and a metallic atom exhibits superior characteristics as a contrast medium for image diagnosis.

12 Claims, 1 Drawing Sheet

CHELATING AGENT, COMPLEX COMPOUND OF SAID CHELATING AGENT AND METALLIC ATOM, AND DIAGNOSTIC AGENT COMPRISING SAME

This is a continuation of application Ser. No. 08/204,164 filed Mar. 3, 1994, now U.S. Pat. No. 5,453,264.

TECHNICAL FIELD

The present invention relates to a chelating agent, a complex compound of said chelating agent and a metallic atom and a diagnostic agent containing said complex compound. More particularly, the present invention relates to a novel metallic chelating agent capable of forming a complex compound with a metallic atom, a complex compound of said chelating agent and a metallic atom which is useful for medical diagnosis, and a diagnostic agent containing said complex compound.

BACKGROUND ART

An image diagnosis which is based on images conveying the information of a lesion is an indispensable method for clinical diagnosis. In addition to an X-ray CT which is one of the image diagnoses currently in wide use, new distinguished techniques for image diagnosis such as Magnetic Resonance Imaging (MRI) have been developed for the last decade or so, and are making great contribution to the development of image diagnosis.

MRI has been recently introduced into the medical field and rapidly improved to be widely used ever since. MRI is advantageously characterized in that it is free of exposure since it does not involve radiation, that optional cross section can be put into an image and that it is free of hindrance by bones, and these characteristics make MRI distinct from conventional X-ray CT. MRI shows magnetic resonance phenomena [usually a relaxation time $(T_1, T_2)$ of hydrogen atomic nucleus] of internal substances with different signal intensities. A paramagnetic substance promotes relaxation of proton (proton of water) and acts as a contrast medium capable of enhancing contrast of images. In particular, rare earth 6d (trivalent) has 7 unpaired electrons on the 4f orbit and has many coordinations (9 or 10), which results in a strong relaxation effect to provide a powerful contrast medium [R. B. Lauffer, *Chem. Rev.*, 87, 901 (1987)]. However, 6d (trivalent) is not discharged from the body and poses toxicity problem.

For this reason, Gd is administered as a complex compound (Gd-DTPA) with a known chelating agent DTPA (diethylenetriaminepentaacetic acid).

Gd-DTPA has been acknowledged to be useful for clinical diagnosis. However, there are many problems to be resolved with respect to Gd-DTPA. For example, the drug per se has a short half-life in blood and poor tissue selectivity and shows a high osmotic pressure since it is present as a bivalent anion complex under physiological conditions. While various approaches have been taken to overcome these problems (Japanese Patent Unexamined Publication Nos. 93758/1988, 1395/1989), they have not necessarily achieved satisfactory results.

Accordingly, research and development of new complex compounds, particularly of a chelating agent, is significantly important.

SUMMARY OF THE INVENTION

An object of the present invention is to provide a novel chelating agent capable of forming a complex compound characterized in that it exhibits superior contrast enhancement, tissue selectivity, stability and duration in blood, and it does not show high osmotic pressure, a complex compound comprising said chelating agent and a metallic atom, and a diagnostic agent containing said complex compound.

With the aim of solving the aforementioned problems, the present inventors have made intensive studies and found that a complex compound of a compound of the following formula (I) and a metallic atom shows superior contrast enhancement, tissue selectivity, stability and duration in blood and does not show high osmotic pressure, which resulted in the completion of the invention. That is, the present invention relates to a compound of the following formula (I) [hereinafter sometimes referred to as Compound (I) or merely as a chelating agent], its salt, a complex compound of the Compound (I) and a metallic atom, its salt and a diagnostic containing said complex compound or its salt.

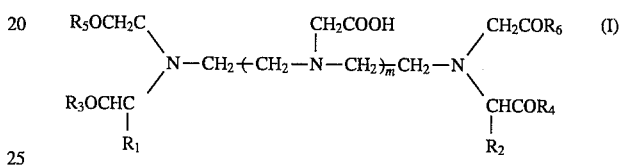

wherein:

m is an integer of 1 to 3;

$R_1$ and $R_2$ are the same or different and each is hydrogen atom or lower alkyl; and $R_3$, $R_4$, $R_5$ and $R_6$ are the same or different and each is hydroxy or a group of the formula

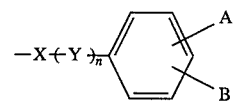

wherein:

n is 0 or 1;

X is —NH— or —O—;

Y is alkylene;

A is hydrogen atom, lower alkyl, lower alkoxy, halogen atom or trifluoromethyl; and B is alkyl or alkenyl, with the proviso that two or three of $R_3$, $R_4$, $R_5$ and $R_6$ are hydroxyl groups and that when two of them are hydroxyl groups, the cases where $R_3$ and $R_5$ are hydroxy, and $R_4$ and $R_6$ are hydroxy are excluded.

DETAILED DESCRIPTION OF THE INVENTION

Figure 1:
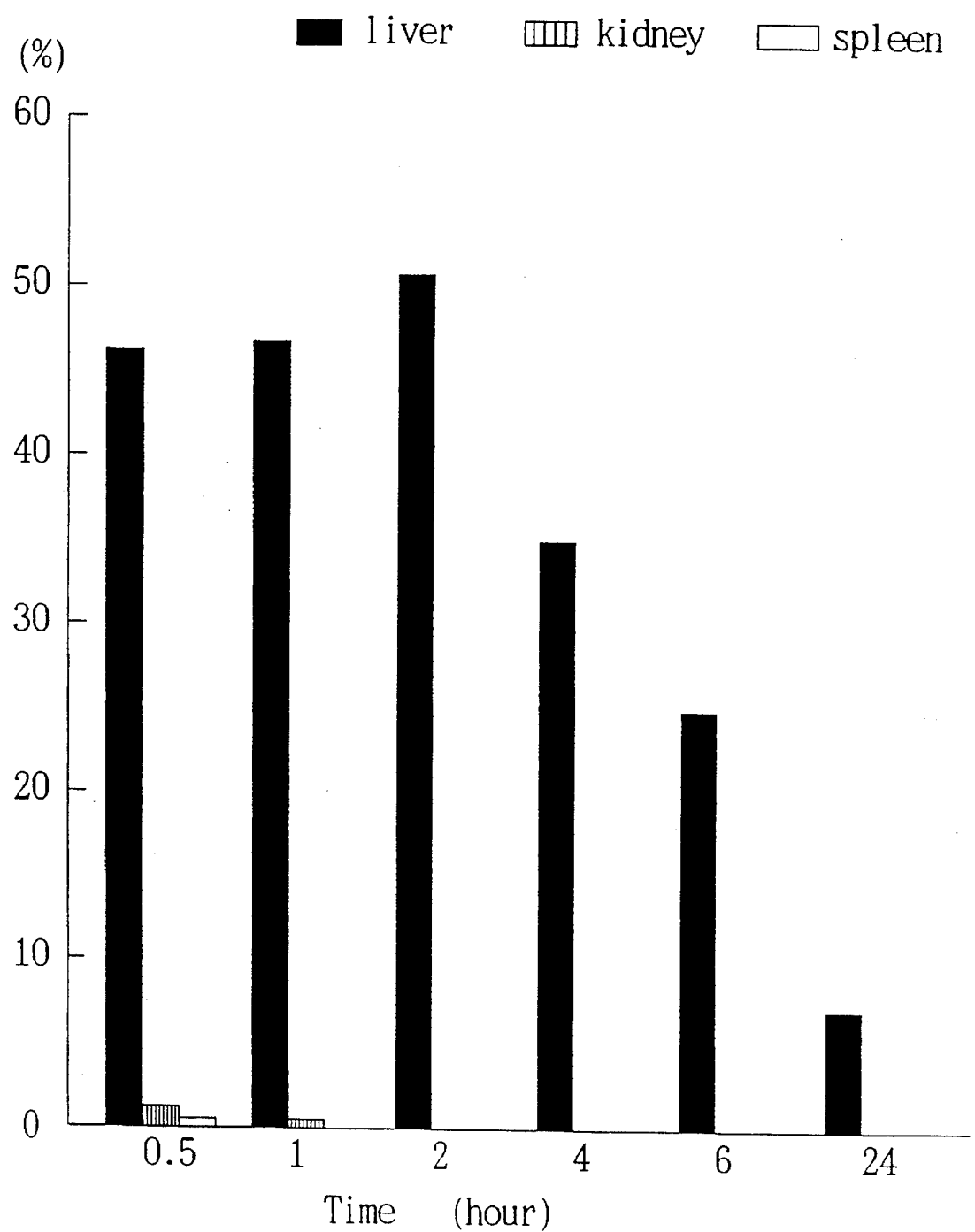
FIG. 1 shows accumulation, in an organ (liver, kidney or spleen), of the complex compound of the present invention comprising a chelating agent and a metallic atom when administered to rats.

In the compounds of the above-depicted formula, lower alkyl may be straight- or branched chain and preferably has 1 to 4 carbon atoms, which is exemplified by methyl, ethyl, propyl, isopropyl, butyl, isobutyl, sec-butyl and tert-butyl.

Alkylene may be straight- or branched chain and preferably has 1 to 10 carbon atoms, which is exemplified by methylene, ethylene, trimethylene, propylene, tetramethylene, pentamethylene, 1-methylethylene, 1-methyltetramethylene, hexamethylene, octamethylene and decamethylene.

Lower alkoxy may be straight- or branched chain and preferably has 1 to 4 carbon atoms, which is exemplified by methoxy, ethoxy, propoxy, butoxy and tert-butoxy.

Alkyl may be straight- or branched chain and preferably has 1 to 20 carbon atoms, which is exemplified by methyl, ethyl, propyl, isopropyl, butyl, isobutyl, sec-butyl, tert-butyl, pentyl, hexyl, octyl, decyl, dodecyl, tetradecyl and octadecyl.

Alkenyl may be straight- or branched chain and preferably has 2 to 20 carbon atoms, which is exemplified by hexenyl, octenyl, 3,7-dimethyl-2,6-dioctadienyl and 9-octadecenyl, with no limitation on the position and the number of double bond.

Halogen atom is exemplified by chlorine atom and bromine atom.

Of the compounds of the formula (I), preferred are those having a total carbon number of Y and B of 5 or more, more preferably 8–12. While there is no limitation on the bonding site of A and B which are the substituents on phenyl, B is preferably bonded at the meta- or para position relative to Y.

Preferably, the salts of the compound of the present invention are pharmaceutically acceptable ones and are exemplified by salts with metal such as sodium and potassium, salts with organic base such as ethanolamine, morpholine and meglumine (N-methylglucamine), and salts with amino acid such as arginine and ornithine.

The compounds of the present invention can be produced by various methods and they are obtainable, for example, by the method shown by the following reaction formulas.

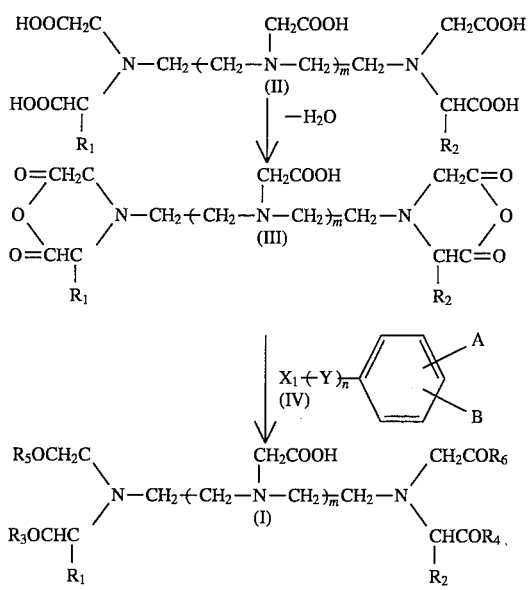

wherein m, n, $R_1$, $R_2$, $R_3$, $R_4$, $R_5$, $R_6$, Y, A and B are as defined above and $X_1$ is —$NH_2$ or —OH.

In the reaction step as described, Compound (III) which is an acid anhydride can be obtained by, for example, subjecting a Compound (II) to a known dehydration using acetic anhydride, dicyclohexylcarbodiimide, 1,1'-carbonyldiimidazole or the like.

The reaction proceeds in a solvent which does not adversely affect the reaction at about 50°–100° C. for about 3 hours to 3 days.

Compound (I) is obtained by reacting a compound (III) and a compound (IV). The reaction between the compound (III) and the compound (IV) can be carried out according to a conventional method including reaction of an acid anhydride and an amino compound or a hydroxyl compound. For example, a compound (III) is dissolved in an organic solvent such as N,N-dimethylformamide (DMF) and a compound (IV) is added thereto upon dissolution in an organic solvent such as methylene chloride or chloroform on demand, followed by reaction at about room temperature to 90° C. for about 30 minutes to 5 days. During this reaction, a basic compound such as pyridine, triethylamine or N,N-dimethylaniline may be added.

When a Compound (I) wherein two of $R_3$–$R_6$ are hydroxyl groups is desired, a compound (IV) is used in 2.0 to 2.3 equivalents relative to a compound (III). When a compound having three hydroxyl groups is desired, a compound (IV) is used in 1.0 to 1.3 equivalents relative to a compound (III). In the latter case wherein hydroxyl groups are three, water (about 1.0 equivalent) is added after the reaction and a reaction under the same reaction conditions as above is carried out, thereby to hydrate the unreacted anhydrous carboxylic acid moiety to introduce same into a Compound (I). The addition of water to the anhydrous carboxylic acid moiety may be performed with the compound (III) prior to the reaction between the compound (III) and the compound (IV).

The salts of the Compound (I) can be prepared according to conventional methods.

The Compound (I) and its salt thus obtained are isolated and purified by a conventional method such as recrystallization, reprecipitation and column chromatography.

The complex compound of the present invention comprises the aforementioned Compound (I) and a metallic atom and preparation of the complex compound can be done by a method known in the pertinent field. For example, an oxide or halide compound of a metal is added to water and treated with an equimolar amount of the Compound (I) or its salt. The Compound (I) and its salt can be added as an aqueous solution. When solubility in water may be low, an organic solvent such as methanol, ethanol, acetone or dimethylsulfoxide may be added. Where necessary, a dilute acid or a dilute base is added for pH control. Heating and cooling involved when preparing a complex compound may be done as appropriate. Pharmaceutically acceptable salts of the complex compound of the present invention are prepared by neutralizing the complex compound with an acid such as an organic acid or an inorganic acid, or a base such as alkali metal hydroxide or basic amino acid, while the complex compound is still in a dissolution state.

The diagnostic agent of the present invention comprises the aforementioned complex compound or its salt and can be used as an MRI diagnostic, X-ray diagnostic, nuclear medicine diagnostic or ultrasonic diagnostic, according to metallic atom selected as appropriate. Particularly preferably, it is used as an MRI diagnostic. In this case, preferable metallic atoms for the complex compound are the elements of atomic number 21–29, 42, 44, and 57–70. The central metallic ion of the complex compound needs to be paramagnetic and bivalent, and trivalent ions of the aforementioned metallic atoms are preferable. Examples of suitable ion include chromium manganese (II), iron (III), cobalt (II), nickel (II), copper (II), praseodymium (III), neodymium (III), samarium (III), gadolinium (III), terbium (III), dysprosium (III), holmium (III), erbium (III) and ytterbium (III) ions, with particular preference given to gadolinium (III), terbium (III), dysprosium (III), holmium (III), erbium (III) and iron (III) ions.

When used as a nuclear medicine diagnostic, the metallic atom of the complex compound needs to be radioactive and, for example, a radioisotope of an element such as gallium, technetium, indium or yttrium is used.

When used as an X-ray diagnostic, the metallic atom of the complex compound needs to absorb X-rays and, for example, a metal of lanthanum series, tantalum or the like is used. These complex compounds are usable as ultrasonic diagnostics.

The diagnostic agent of the present invention is provided in the form of an aqueous solution, emulsion, liposome preparation or a lyophilized preparation thereof, which are prepared by conventional means for producing pharmaceutical preparations from an aqueous solution of the aforementioned complex compound. When in use, the lyophilized preparation is dissolved or dispersed in a suitable diluent. The diagnostic agent of the present invention may contain physiologically acceptable buffer such as tris(hydroxymethyl)aminomethane or other physiologically acceptable additives such as stabilizer (e.g. p-hydroxybenzoate esters). The diagnostic agent of the present invention can be used in the same manner as when using other conventional diagnostic agents and, for example, a liquid preparation is orally or parentorally administered to mammals inclusive of human. The dose is substantially the same as that of the conventional diagnostic agents and is about 0.001–5 mmol/kg, usually about 0.005–0.5 mmol/kg.

The complex compound composed of the compound of the present invention and a metallic atom exhibits superior contrast enhancement, tissue selectivity, safety and duration in blood and does not show high osmotic pressure. Accordingly, it is useful for medical diagnosis, in particular, for MRI diagnosis.

The complex compound of the present invention is advantageously used for imaging various organs such as liver and spleen, tumor, blood vessels etc. and is also useful as a diagnostic agent for arterial sclerosis. The complex compound specifically shows high accumulation in the lesions of atherosclerosis and is useful for the diagnosis of atherosclerosis. Also, the complex compound is useful for the diagnosis of liver tumor. In addition, the compound of the present invention has a benzene ring in the molecule. Therefore, tracing and analysis of internal kinetics and concentration in blood of the complex compound can be easily done using UV absorption (e.g. at 254 nm) as an index. Furthermore, the compound of the present invention is appropriately liposoluble and has affinity for lipids. For this reason, the complex compound of the present invention is easily prepared into a lipid emulsion or liposome by a known method, thus enabling further improvement in tissue selectivity. The preferable compounds are N-(4-octylphenylcarbamoylmethyl)diethylenetriamine-N,N',N'',N''-tetraacetic acid (DTPA-OA, Example 4 to be mentioned later); N-(4-hexylphenylcarbamoylmethyl)diethylenetriamine-N, N',N'',N''-tetraacetic acid (DTPA-HA, Example 5 to be mentioned later); N(4-decylphenylcarbamoylmethyl)diethylenetriamine-N,N',N'',N''-tetraacetic acid (DTPA-DeA, Example 6 to be mentioned later); and N-(4-dodecylphenylcarbamoylmethyl)diethylenetriamine-N,N',N'',N''-tetraacetic acid (DTPA-DoA, Example 7 to be mentioned later).

While the present invention is explained in detail by illustration of Examples and Experimental Examples in the following, the present invention is not limited to them.

EXAMPLE 1

Synthesis of diethylenetriaminepentaacetic acid diamides-1
[A Compound (I) wherein m=1, $R_1=R_2=H$, $R_3=R_4=$p-$C_8H_{17}C_6H_4NH$, $R_5=R_6=OH$, DTPA-DIOA]

Diethylenetriaminepentaacetic acid dianhydride (2.05 g, 5.7 mmol) was dissolved in dry DMF (100 ml). A solution of 4-octylaniline (2.36 g, 11.4 mmol) in methylene chloride (10 ml) was added thereto and the mixture was stirred at room temperature for 15 hours. The resultant crystals were collected by filtration, washed with ether and recrystallized (ethanol:methanol:benzene=6:1:1) to give 3.64 g of the object compound (white amorphous, mp 207.0°–208.5 ° C.), yield 82.7%.

$^1$H-NMR (CDCl$_3$+CF$_3$COOD) δ: 0.88 (6H, t, J=6.4 Hz), 1.2–1.4 (20H, m), 1.5–1.7 (4H, m), 2.57 (4H, t, J=7.6 Hz), 3.2–3.4 (4H, m), 3.6–3.9 (6H, m), 4.33 (4H, s), 4.43 (4H, s), 7.16 (8H, s)

IR (KBr): 3350, 1680, 1620 cm$^{-1}$

EXAMPLE 2

Synthesis of diethylenetriaminepentaacetic acid diamides-2
[A Compound (I) wherein m=1, $R_1=R_2=H$, $R_3=R_4=$p-$C_6H_{13}C_6H_4NH$, $R_5=R_6=OH$, DTPA-DIHA]

Diethylenetriaminepentaacetic acid dianhydride (2.02 g, 5.7 mmol) was dissolved in dry DMF (100 ml). A solution of 4-hexylaniline (2.02 g, 11.4 mmol) in methylene chloride (10 ml) was added thereto and the mixture was stirred at room temperature for 15 hours. The solvent was distilled away and the residue was crystallized with ether and recrystallized (THF: methanol=3:1) to give 3.36 g of the object compound (white amorphous, mp 207.5°–209.0° C.), yield 82.8%.

$^1$H-NMR (CDCl$_3$+CF$_3$COOD) δ: 0.88 (6H, t, J=6.2 Hz), 1.2–1.4 (12H, m), 1.5–1.7 (4H, m), 2.58 (4H, t, J=7.7 Hz ), 3.2–3.4 (4H, m), 3.7–3.9 (6H, m), 4.34 (4H, s), 4.44 (4H, s), 7.17 (8H, s)

IR (KBr): 3330, 1680, 1620 cm$^{-1}$

EXAMPLE 3

Synthesis of triethylenetetraminehexaacetic acid diamides
[A Compound (I) wherein m=2, $R_1=R_2=H$, $R_3=R_4=$p-$C_6H_{17}C_6H_4NH$, $R_5=R_6=OH$, TTHA-DIOA]

Triethylenetetraaminehexaacetic acid dianhydride (1.20 g, 2.6 mmol, obtained from triethylenetetraaminehexaacetic acid by conventional dehydration using acetic anhydride and anhydrous pyridine) was dissolved in dry DMF (120 ml). A solution of 4-octylaniline (1.04 g, 5.1 mmol) in methylene chloride (10 ml) was added thereto and the mixture was stirred at room temperature for 4 days. The resultant crystals were collected by filtration, washed with ether and then with ethanol and recrystallized (THF:methanol=3:1) to give 1.55 g of the object compound (white amorphous, mp 212.5°–214.0° C.), yield 68.0%.

$^1$H-NMR (CDCl$_3$+CF$_3$COOD) δ: 0.88 (6H, t, J=6.4 Hz), 1.2–1.4 (20H, m), 1.5–1.7 (4H, m), 2.59 (4H, t, J=7.7 Hz), 3.4–3.8 (8H, m), 3.8–4.1 (8H, m), 4.36 (4H, m), 4.50 (4H, m), 7.19 (8H, s)

IR (KBr): 3600–3200, 1720, 1670 cm$^{-1}$

EXAMPLE 4

Synthesis of diethylenetriaminepentaacetic acid monoamides-1
[A Compound (I) wherein m=1, $R_1=R_2=H$, $R_3=$p-$C_8H_{17}C_6H_4NH$, $R_4=R_5=R_6=OH$, DTPA-OA]

Diethylenetriaminepentaacetic acid dianhydride (3.00 g, 8.4 mmol) was dissolved in dry DMF (45 ml) at 75° C. Water (0.15 ml, 8.3 mmol) was dropwise added thereto and the mixture was stirred at said temperature for 1 hour to produce diethylenetriaminepentaacetic acid monoanhydride. 4-Octylaniline (1.75 g, 8.3 mmol) was dropwise added there to and the mixture was stirred at said temperature for 1 hour. The mixture was purified by column chromatography (eluate: 40% aqueous methanol) to give 1.48 g of the object compound (white amorphous, mp 164.0°–167.0° C.), yield 30.0%.

$^1$H-NMR (CD$_3$OD+CF$_3$COOD) δ: 0.89 (3H, t, J=6.4 Hz), 1.1–1.5 (10H, m), 1.5–1.7 (2H, m), 2.56 (2H, t, J=7.5 Hz), 3.1–3.4 (4H, 3.4–3.6 (4H, m), 3.6–3.9 (8H, m), 4.36 (2H, s), 7.13 (2H, d, J=8.4 Hz), 7.49 (2H, d, J=8.4 Hz)

IR (KBr): 3400–3000, 1680, 1610 cm$^{-1}$

EXAMPLE 5

Synthesis of diethylenetriaminepentaacetic acid monoamides-2

[A Compound (I) wherein m=1, R$_1$=R$_2$=H, R$_3$=p-C$_6$H$_{13}$C$_6$H$_4$NH, R$_4$=R$_5$=R$_6$=OH, DTPA-HA]

Diethylenetriaminepentaacetic acid dianhydride (3.00 g, 8.4 mmol) was dissolved in dry DMF (45 ml) at 75° C. Water (0.15 ml, 8.3 mmol) was dropwise added thereto and the mixture was stirred at said temperature for 1 hour to produce diethylenetriaminepentaacetic acid monoanhydride. 4-Hexylaniline (1.47 g, 8.3 mmol) was dropwise added thereto and the mixture was stirred at said temperature for 1 hour. The mixture was purified by column chromatography (eluate: 20% aqueous methanol) to give 1.74 g of the object compound (slightly yellow amorphous, mp 159.0°–160.0° C.), yield 38.0%.

$^1$H-NMR (CD$_3$OD) δ: 0.89 (3H, t, J=6.5 Hz), 1.2–1.5 (6H, m), 1.5–1.8 (2H, m), 2.55 (2H, t, J=7.5 Hz), 3.1–3.5 (8H, m), 3.60 (2H, brs), 3.68 (6H, brs), 3.79 (2H, brs), 7.11 (2H, d, J=8.4 Hz), 7.53 (2H, d, J=8.4 Hz)

IR (KBr): 3380–3000, 1680, 1610 cm$^{-1}$

EXAMPLE 6

Synthesis of diethylenetriaminepentaacetic acid monoamides-3

[A Compound (I) wherein m=1, R$_1$=R$_2$=H, R$_3$=p-C$_{10}$H$_{21}$C$_6$H$_4$NH, R$_4$=R$_5$=R$_6$=OH, DTPA-DeA]

Diethylenetriaminepentaacetic acid dianhydride (3.97 g, 11.1 mmol) was dissolved in dry DMF (60 ml) at 75° C. Water (0.20 ml, 11.1 mmol) was dropwise added thereto and the mixture was stirred at said temperature for 1 hour to produce diethylenetriaminepentaacetic acid monoanhydride. A solution of 4-decylaniline (2.59 g, 11.1 mmol) in dry methylene chloride (5 ml) was dropwise added thereto and the mixture was stirred at said temperature for 1 hour. The mixture was purified by column chromatography (eluate: 40% aqueous methanol) to give 3.06 g of the object compound (white amorphous, mp 169.0°–172.0° C.), yield 45.3%.

$^1$H-NMR (CD$_3$OD) δ: 0.89 (3H, t, J=6.3 Hz), 1.2–1.4 (14H, m), 1.5–1.7 (2H, m), 2.56 (2H, t, J=7.5 Hz), 3.1–3.4 (8H, m), 3.59 (2H, s), 3.63 (4H, s), 3.71 (2H, s), 3.73 (2H, s), 7.12 (2H, d, J=8.3 Hz), 7.53 (2H, d, J=8.3 Hz)

IR (KBr): 3500–3000, 1680, 1620 cm$^{-1}$

EXAMPLE 7

Synthesis of diethylenetriaminepentaacetic acid monoamides-4

[A Compound (I) wherein m=1, R$_1$=R$_2$=H, R$_3$=p-C$_{12}$H$_{25}$C$_6$H$_4$NH, R$_4$=R$_5$=R$_6$=OH, DTPA-DoA]

Diethylenetriaminepentaacetic acid dianhydride (3.97 g, 11.1 mmol) was dissolved in dry DNF (60 ml) at 75° C. Water (0.20 ml, 11.1 mmol) was dropwise added thereto and the mixture was stirred at said temperature for 1 hour to produce diethylenetriaminepentaacetic acid monoanhydride. A solution of 4-dodecylaniline (2.91 g, 11.1 mmol) in dry methylene chloride (5 ml) was dropwise added thereto and tile mixture was stirred at said temperature for 1 hour. The mixture was purified by column chromatography (eluate: 40% aqueous methanol) to give 2.60 g of the object compound (white amorphous, mp 171.0°–173.5° C.), yield 36.7%.

$^1$H-NMR (CD$_3$OD) δ: 0.89 (3H, t, J=6.4 Hz), 1.2–1.4 (16H, m), 1.5–1.7 (2H, m), 2.56 (2H, t, J=7.5 Hz), 3.1–3.4 (8H, m), 3.50 (2H, s), 3.61 (2H, s), 3.66 (4H, s), 3.71 (2H, s), 7.11 (2H, d, J=8.4 Hz), 7.54 (2H, d, J=8.4 Hz)

IR (KBr): 3500–3000, 1680, 1620 cm$^{-1}$

EXAMPLE 8

Synthesis of triethylenetetraaminehexaacetic acid monoamides-1

[A Compound (I) wherein m=2, R$_1$=R$_2$=H, R$_3$=p-C$_8$H$_{17}$C$_6$H$_4$NH, R$_4$=R$_5$=R$_6$=OH, TTHA-OA]

Triethylenetetraaminehexaacetic acid dianhydride (4.63 g, 10.1 mmol) was dissolved in dry DMF (55 ml) at 80° C. Water (0.18 ml, 10 mmol) was dropwise added thereto and the mixture was stirred at said temperature for 30 minutes to produce triethylenetetraaminehexaacetic acid monoanhydride. 4-Octylaniline (2.3 ml, 10.1 mmol) was dropwise added thereto and the mixture was stirred at said temperature for 1 hour. The mixture was purified by HPLC (eluate: 35% aqueous methanol) to give 2.28 g of the object compound (brown amorphous, mp 182°–184° C.), yield 33%.

$^1$H-NMR (CD$_3$OD) δ: 0.89 (3H, t, J=6.4 Hz), 1.1–1.45 (10H, m), 1.45–1.7 (2H, m), 2.56 (2H, t, J=7.5 Hz), 2.9–3.25 (6H, m), 3.25–3.55 (10H, m), 3.57 (2H, s), 3.65–3.9 (6H, m), 7.11 (2H, d, J=8.4 Hz), 7.55 (2H, d, J=8.4 Hz) IR (KBr): 3400, 1620 cm$^{-1}$

EXAMPLE 9

Synthesis of triethylenetetraaminehexaacetic acid monoamides-2

[A Compound (I) wherein m=2, R$_1$=R$_2$=H, R$_3$=p-C$_6$H$_{13}$C$_6$H$_4$NH, R$_4$=R$_5$=R$_6$=OH, TTHA-HA]

Triethylenetetraaminehexaacetic acid dianhydride (500 mg, 1.1 mmol) was dissolved in dry DMF (10 ml) at 80° C. Water (0.02 ml, 1.1 mmol) was dropwise added thereto and the mixture was stirred at said temperature for 1 hour to produce triethylenetetraaminehexaacetic acid monoanhydride. 4-Hexylaniline (0.18 g, 1.0 mmol) was dropwise added thereto and the mixture was stirred at said temperature for 1 hour. The mixture was purified by column chromatography (eluate: 20% aqueous methanol) to give 119 mg of the object compound (anhydrous amorphous, mp 168.0°–170.0° C.), yield 18.0%.

$^1$H-NMR (CD$_3$OD) δ: 0.89 (3H, t, J=6.4 Hz), 1.2–1.5 (6H, m), 1.5–1.7 (2H, m), 2.57 (2H, t, J=7.5 Hz), 3.0–3.3 (6H, m), 3.3–3.5 (6H, m), 3.5–3.6 (4H, m), 3.61 (2H, s), 3.7–3.9 (6H, m), 7.11 (2H, d, J=8.4 Hz), 7.54 (2H, d, J=8.4 Hz)

IR (KBr): 3380–3000, 1680, 1610 cm$^{-1}$

EXAMPLE 10

Synthesis of diethylenetriaminepentaacetic acid diesters-1
[A Compound (I) wherein m=1, R$_1$=R$_2$=H, R$_3$R$_4$=p-C$_4$H$_9$C$_6$H$_4$CH$_2$O, R$_5$=R$_6$=OH]

Diethylenetriaminepentaacetic acid dianhydride (1.43 g, 4.00 mmol) was dissolved in dry (24 ml) at 80° C. A solution of 4-butylbenzyl alcohol (1.32 g, 8.00 mmol) in dry DMF (12 ml) was added thereto and the mixture was stirred at said temperature for 16 hours. The solvent was distilled away and the residue was recrystallized (chloroform-hexane) to give 2.04 g of the object compound (white amorphous, mp 61.5°–63.5° C.), yield 74.5%.

$^1$H-NMR (CDCl$_3$) δ: 0.90 (6H, t, J=7.2 Hz), 1.2–1.4 (4H, m), 1.5–1.6 (4H, m), 2.56 (4H, t, J=7.6 Hz), 3.0–3.2 (4H, m), 3.3–3.7 (12H, m), 4.0–4.2 (2H, m), 5.02 (4H, s ), 7.10 (4H, d, J=8.1 Hz), 7.19 (4H, d, J=8.1 Hz)

IR (KBr): 3400, 1730, 1620 cm$^{-1}$

EXAMPLE 11

Synthesis of diethylenetriaminepentaacetic acid diesters-2 [A Compound (I) wherein m=1, R$_1$=R$_2$=H, R$_3$=R$_4$=p-C$_{13}$H$_{27}$C$_6$H$_4$CH$_2$O, R$_5$=R$_6$=OH]

In the same manner as in Example 10 except that 4-tridecylbenzyl alcohol (synthesized by conventional method) was used in place of 4-butylbenzyl, alcohol, the object compound (pale yellow amorphous, mp 157.0°–161.0° C.) was obtained.

$^1$H-NMR (CDCl$_3$+CF$_3$COOD) δ: 0.87 (6H, t, J=6.3 Hz), 1.2–1.4 (40H, m), 1.5–1.7 (4H, m), 2.56 (4H, t, J=7.4 Hz), 3.1–3.9

(10H, m), 4.0–4.3 (8H, m), 5.12 (4H, brs), 7.15 (8H, t)

IR (KBr): 3400, 1730, 1700, 1620 cm$^{-1}$

EXAMPLE 12

Synthesis of diethylenetriaminepentaacetic acid monoesters [A Compound (I) wherein m=1, R$_1$=R$_2$=H, R$_3$=p-C$_{13}$H$_{27}$C$_6$H$_4$CH$_2$O, R$_4$=R$_5$=R$_6$=OH, DTPA-TBE]

In the same manner as in Example 4 except that 4-tridecylbenzyl alcohol was used in place of 4-octylaniline, the object compound (pale yellow amorphous, mp 194.0°–97.0° C.) was obtained.

$^1$H-NMR (CDCl$_3$+CF$_3$COOD) δ: 0.88 (3H, t, J=6.6 Hz), 1.2–1.4 (20H, m), 1.5–1.7 (2H, m), 2.61 (2H, t, J=7.8 Hz), 3.3–3.4 (4H, m), 3.6–3.8 (4H, m), 3.80 (2H, s), 4.26 (6H, s), 4.31 (2H, s), 5.22 (2H, s), 7.21 (4H, s)

IR (KBr): 3400, 1720, 1700, 1630 cm$^{-1}$

EXAMPLE 13

Preparation of Gd. DTPA-OA complex compound

To an aqueous solution of DTPA-OA (5.8 g) obtained by the method of Example 4 in distilled water (800 ml) was gradually added a 0.05 M GdCl$_3$ solution (200 ml) and the mixture was stirred while adjusting its pH to about 7.0 with 0.1N aqueous solution of NaOH, followed by reaction at room temperature for about 1 hour. After the reaction, the reaction mixture was lyophilized to give 7.92 g of Gd•DTPA-OA complex compound.

EXAMPLE 14

Preparation of Gd•DTPA-DeA complex compound

In the same manner as in Example 13 except that DTPA-DeA obtained by the method of Example 6 was used in place of DTPA-OA, the object complex compound was obtained.

EXAMPLE 15

Preparation of lipid-emulsified complex compound

Purified egg yolk phospholipid (60 g) and Gd•DTPA-DeA complex compound (40 g) were added to purified soybean oil (100 g) and mixed. Distilled water (1750 ml) and glycerin (20.0 g) were added thereto and the mixture was homogenized in a homomixer. The mixture was subjected to high-pressure emulsification in a Manton-Gaulin high pressure homogenizer to give a homogenized highly fine Gd•DTPA-DeA lipid emulsion having an average particle size of not more than 1 μm. The osmotic pressure of the obtained Gd•DTPA-DeA lipid emulsion to physiological saline was about 1.0.

Experimental Example 1

Diagnosis of atherosclerosis using complex compound of the invention

Rabbit models with arterial sclerosis were fixed at the dorsal position without anesthetizing and an aqueous solution of Gd•DTPA-OA as obtained in Example 13 was continuously administered to the rabbits at 2 ml/min from the auricular vein at a dose of 200 μmol/kg. The rabbits were poisoned to death at 5 min, 30 min or 6 hours after the administration and the thoracica aorta was removed. The fat adhered to the outside of the aorta was carefully removed and the blood vessel was incised to remove the sclerosis lesion. The lesion was placed in an NMR test tube and subjected to NRI imaging. The NRI system was Siemens Magnetom 1.ST and the coil used was an eye coil. Image pickup was done at time of repetition (TR)=500 msec, echo time (TE)=22 msec, slice thickness=1 mm, accumulation=8 times and matrix=128×256.

The obtained image clearly showed the sclerosis lesion in the blood vessel with distinct contrast between the sclerosis lesion and where not, thus proving its usefulness as a contrast medium for MRI diagnosis.

Experimental Example 2

Measurement of internal distribution in rat organs

An aqueous solution of Gd•DTPA-DoA as obtained by the procedure similar to that in Example 13 was bolus-administered at 0.02 mmol/kg from the tail vein. The test animal was slaughtered with CO$_2$ gas at 30 min, 1 hour, 2 hours, 4 hours, 6 hours or 24 hours after the administration and dehematized. Organs (liver, kidney and spleen) were removed. After homogenizing each organ, ethanol was added thereto and the mixture was centrifuged to give a supernatant. The supernatant was subjected to HPLC (65% methanol, 1% triethylamine, pH 7.0, C18 column) to measure the amount of the complex compound and the percentage thereof to the dose was calculated. The results are shown in FIG. 1. As shown in FIG. 1, a superior accumulation in liver was found.

What is claimed:

1. A compound of the following formula (I)

$$R_5OCH_2C\diagdown_{R_3OCHC\atop |\atop R_1}\diagup N-CH_2(CH_2-N-CH_2)_{\overline{m}}CH_2-N\diagup^{CH_2COOH}\diagdown_{CHCOR_4\atop |\atop R_2}^{CH_2COR_6} \quad (I)$$

wherein:

m is an integer of 1 to 3;

R$_1$ and R$_2$ are the same or different and each is hydrogen atom or lower alkyl; and $R_3$, $R_4$, $R_5$ and $R_6$ are the same or different and each is hydroxy or a group of the formula

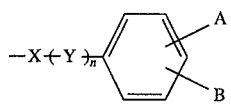

wherein:
n is 0 or 1;
x is —NH— or —O—;
Y is alkylene;
A is hydrogen atom, lower alkyl, lower alkoxy, halogen atom or trifluoromethyl; and
B is alkyl or alkenyl, the total carbon number of Y and B is 5 to 7;
with the proviso that two or three of $R_3$, $R_4$, $R_5$ and $R_6$ are hydroxyl groups and that when two of them are hydroxyl groups, the cases where $R_3$ and $R_5$ are hydroxy, and $R_4$ and $R_6$ are hydroxy are excluded; or a salt thereof.

2. The compound of claim 1 wherein, in the formula (I), the total carbon number of Y and B is 6.

3. The compound of claim 1 wherein, in the formula (I), B is bonded at the meta- or para position relative to Y, or a salt thereof.

4. The compound of claim 13 which is N-(4-hexylphenylcarbamoylmethyl)diethylenetriamine-N,N',N'',N''-tetraacetic acid, or a salt thereof.

5. A complex consisting essentially of the compound of claim 1 as a chelating compound coordinately bound to a metallic atom, or a salt thereof.

6. The complex of claim 5, wherein the metallic atom is a paramagnetic metallic atom, or a salt thereof.

7. The complex of claim 6, wherein the metallic atom is selected from the group consisting of gadolinium (III), terbium (III), dysprosium (III), holmium (III), erbium (III) and iron (III).

8. A pharmaceutical composition comprising the complex of claim 5 or a salt thereof.

9. The composition of claim 8 which is a diagnostic agent.

10. A diagnostic agent for arterial sclerosis, comprising a complex comprising the compound of claim 1 as a chelating compound coordinately bound to a paramagnetic metallic atom, or a salt thereof.

11. A diagnostic agent for liver tumor, comprising a complex comprising the compound of claim 1 as a chelating compound coordinately bound to a paramagnetic metallic atom, or a salt thereof.

12. A method for image diagnosis, comprising administering a complex comprising the compound of claim 1 as a chelating compound coordinately bound to a metallic atom, or a salt thereof to a patient with a potential disease, and imaging a lesion.

* * * * *

UNITED STATES PATENT AND TRADEMARK OFFICE
CERTIFICATE OF CORRECTION

PATENT NO. : 5,575,986
DATED : November 19, 1996
INVENTOR(S) : Fumio MORI, et al.

It is certified that error appears in the above-indentified patent and that said Letters Patent is hereby corrected as shown below:

On the title page:

Item: [75] Inventors: delete "Sang-Won Kim" and insert --Shogen Kindaichi--.

Item: [75] Inventors: after "Taro Marukawa," delete "Nagoya" and insert --Osaka-- .

Signed and Sealed this

Twenty-second Day of April, 1997

*Attest:*

BRUCE LEHMAN

*Commissioner of Patents and Trademarks*

*Attesting Officer*